US010709841B2

(12) United States Patent
Cowe et al.

(10) Patent No.: US 10,709,841 B2
(45) Date of Patent: Jul. 14, 2020

(54) INJECTION DEVICE

(71) Applicant: Owen Mumford Limited, Brook Hill, Woodstock, Oxford, Oxfordshire (GB)

(72) Inventors: Toby Cowe, Oxfordshire (GB); Matthew Farmer, Oxfordshire (GB)

(73) Assignee: Owen Mumford Limited, Oxford (GB)

( * ) Notice: Subject to any disclaimer, the term of this patent is extended or adjusted under 35 U.S.C. 154(b) by 153 days.

(21) Appl. No.: 15/766,608

(22) PCT Filed: Oct. 12, 2016

(86) PCT No.: PCT/GB2016/053161
§ 371 (c)(1),
(2) Date: Apr. 6, 2018

(87) PCT Pub. No.: WO2017/064483
PCT Pub. Date: Apr. 20, 2017

(65) Prior Publication Data
US 2018/0296761 A1 Oct. 18, 2018

(30) Foreign Application Priority Data
Oct. 12, 2016 (GB) .................................. 1518021.9

(51) Int. Cl.
*A61M 5/20* (2006.01)
*A61M 5/315* (2006.01)
*A61M 5/32* (2006.01)

(52) U.S. Cl.
CPC ...... *A61M 5/2033* (2013.01); *A61M 5/31583* (2013.01); *A61M 5/326* (2013.01);
(Continued)

(58) Field of Classification Search
CPC .. A61M 5/20; A61M 5/2033; A61M 5/31583; A61M 5/326; A61M 5/31585;
(Continued)

(56) References Cited

U.S. PATENT DOCUMENTS

2013/0289525 A1* 10/2013 Kemp ................. A61M 5/2033
604/506
2014/0330214 A1* 11/2014 Olson ..................... A61M 5/20
604/189
2014/0330216 A1 11/2014 Weaver et al.

FOREIGN PATENT DOCUMENTS

GB 2507541 A 5/2014
GB 2516624 A 2/2015
(Continued)

OTHER PUBLICATIONS

Feb. 8, 2017 Transmittal of ISR and Written Opinion of International Searching Authority for PCT/GB2016/053161.

*Primary Examiner* — Kami A Bosworth
*Assistant Examiner* — Antarius S Daniel
(74) *Attorney, Agent, or Firm* — Quarles & Brady LLP

(57) ABSTRACT

An injection device (100) suitable for the delivery of a viscous medicament from a container (10) through a needle (16) disposed at the distal end of the container (10) is disclosed. The device comprises a housing (102), an advancing mechanism (190, 204, 230) operable to move the container (10) relative to the housing from a starting position in which the needle (16) is shrouded and an insertion position in which the needle (16) is exposed, and a stopper drive arrangement operable to move a stopper (22) towards the distal end of the container (10). The stopper drive arrangement comprises a drive body (240) arranged for axial movement with respect to the housing (102), a driveshaft (250) arranged for rotation with respect to the drive body (240), a plunger (202) arranged for axial movement with respect to the drive body (240) to move the stopper (22) upon rotation of the driveshaft (250), and drive means (290) arranged to rotate the driveshaft (250) upon activation of the stopper drive arrangement.

35 Claims, 10 Drawing Sheets

(52) U.S. Cl.
CPC ..... *A61M 5/3204* (2013.01); *A61M 2005/206* (2013.01); *A61M 2005/2013* (2013.01); *A61M 2005/2073* (2013.01)

(58) Field of Classification Search
CPC ............ A61M 5/3232; A61M 5/31525; A61M 2005/206; A61M 2005/2073; A61M 2005/2026; A61M 2005/2006
See application file for complete search history.

(56) References Cited

FOREIGN PATENT DOCUMENTS

| | | | |
|---|---|---|---|
| WO | WO 2012/049484 A2 | 4/2012 | |
| WO | WO 2012/173553 A1 | 12/2012 | |
| WO | WO 2014/053451 A1 | 4/2014 | |
| WO | WO-2014111371 A1 * | 7/2014 | .......... A61M 5/2033 |
| WO | WO 2015/055640 A1 | 4/2015 | |

* cited by examiner

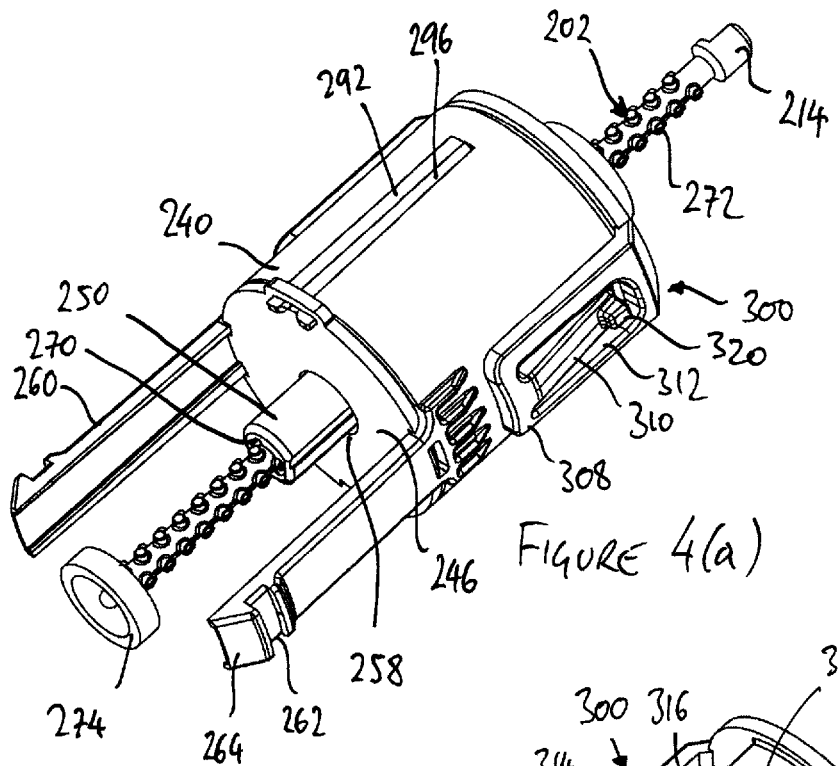
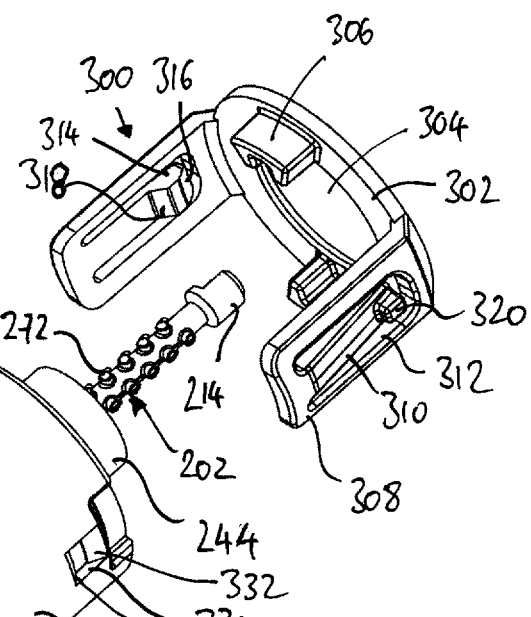
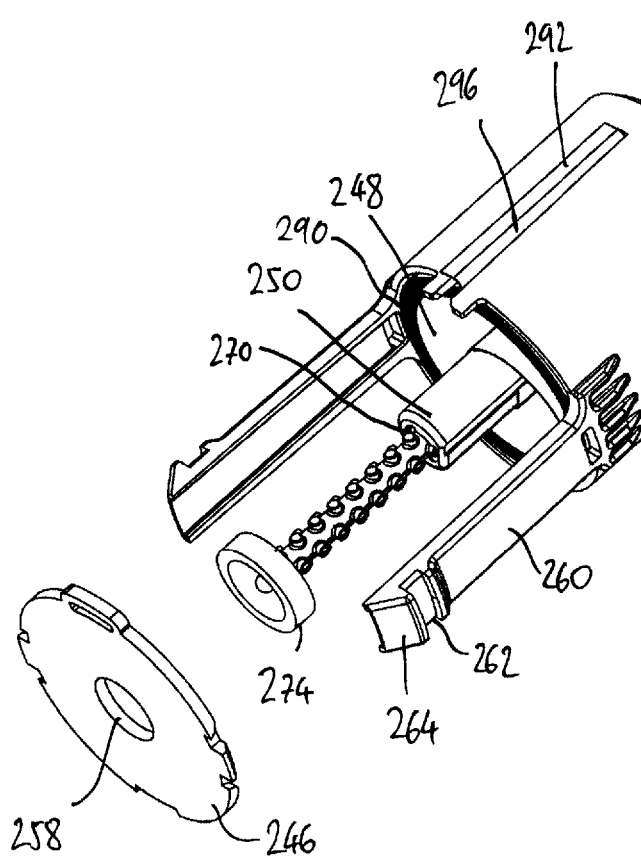
FIGURE 4(a)
FIGURE 4(b)

INJECTION DEVICE

The present application is a § 371 submission of international application no. PCT/GB2016/053161, filed 12 Oct. 2016 and titled Injection Device, which was published in the English language on 20 Apr. 2017 with publication no. WO 2017/064483, and which claims the benefit of the filing date of GB 15 18021.9 filed 12 Oct. 2015, the contents of which are incorporated herein by reference.

The present invention relates to injection devices suitable for the injection of a medicament to a patient. In particular, but not exclusively, the invention relates to auto-injector devices in which activation of the device causes automatic insertion of a needle and delivery of the medicament through the needle.

Injection devices designed for automatic needle insertion and injection of a single pre-determined dose of a medicament are known in the art as auto-injectors. Such devices typically include a housing that allows the user to grip the device, a pre-filled syringe containing the medicament, and a firing mechanism. The pre-filled syringe includes a tubular glass barrel with a staked hypodermic needle at its distal end, a needle shield to protect and seal the needle, and a stopper slidably received in the barrel. One example of a pre-filled syringe of this type is available under the registered trade mark Hypak (Becton Dickinson, N.J., USA).

The firing mechanism typically comprises a plunger that is biased in the distal direction by a compression spring. The plunger is initially held in a starting position by the firing mechanism. Upon activation of the firing mechanism, the plunger is released from the starting position and can move distally under the force of the compression spring.

The syringe is axially movable within the housing between an initial, retracted position in which the needle is retracted in the housing, and a deployed position in which the needle projects from the end of the housing.

With the syringe in the retracted position, the distal end of the housing is closed by a cap. To prepare the device for use, the cap is removed. The cap is arranged to grip the rigid needle shield, so that removal of the cap pulls the rigid needle shield off the needle.

The distal end of the housing is then placed against the skin, and the user operates a trigger of the device, such as a button, to activate the firing mechanism. The spring-biased plunger is released to move in the distal direction. Initially, release of the plunger causes the syringe to move from the retracted position into the deployed position, so that the needle pierces the skin. Subsequently, the plunger forces the stopper in the distal direction to inject the medicament.

Examples of such devices are described in the Applicant's International Patent Application Publication No. WO 2012/049484 and UK Patent Application Publication No. GB 2516624, the contents of which are incorporated herein by reference.

Auto-injectors provide a convenient means for self-administration by a patient of a measured dose of a medicament, although they may also be used by trained medical personnel. In both cases, auto-injectors typically offer increased user safety compared with traditional syringes, for example by ensuring that the needle used to deliver the medicament is shrouded before and/or after delivery of the medicament, and by the inclusion of interlock means or other safety devices to prevent accidental operation of the device.

Because of these advantages, it has become desirable to use auto-injectors for the delivery of a wide range of drugs, including medicaments with relatively high viscosity. However, as the viscosity of the medicament increases, it becomes more difficult to force the medicament through the relatively narrow bore of the needle for injection. Since increasing the diameter of the needle and/or increasing the time taken for injection would be unattractive, it is necessary to apply a greater force to the stopper of the syringe as the viscosity of the medicament increases.

One approach to increasing the force applied by the plunger for the injection of high-viscosity drugs is to use a higher-force compression spring to drive the plunger. However, this approach requires a larger spring, which can be difficult to accommodate without increasing the length of the housing. Furthermore, the increased spring force can result in an increase in the stress applied by the spring to the components of the device, which can cause failure or distortion of plastic parts. Also, the increased impact forces that arise upon activation of the device could cause damage to the glass body of the syringe and increase discomfort for the user.

It would therefore be desirable to provide an injection device capable of automatic needle insertion and medicament delivery that can be used with relatively high-viscosity drugs that avoids or mitigates the above-mentioned problems.

Against this background, in a first aspect of the present invention there is provided an injection device for the delivery of a medicament from a container through a needle disposed at the distal end of the container, the container having a stopper for containing the medicament within the container, the device comprising a housing, an advancing mechanism operable to move the container relative to the housing from a starting position in which the needle is shrouded and an insertion position in which the needle is exposed, and a stopper drive arrangement operable to move the stopper towards the distal end of the container. The stopper drive arrangement comprises a drive body, a driveshaft arranged for rotation with respect to the drive body, a plunger arranged for axial movement with respect to the drive body to move the stopper upon rotation of the driveshaft, and drive means arranged to rotate the driveshaft upon activation of the stopper drive arrangement.

By providing both an advancing mechanism and a stopper drive arrangement, the force applied to move the container for needle insertion can be independent of the force applied to move the stopper of the container for medicament delivery. The drive means of the stopper drive arrangement can therefore be selected to apply a much larger force to the stopper than would be possible if that force was also to be used to insert the needle. Furthermore, because the plunger of the stopper drive arrangement is driven by a rotating driveshaft, the impact forces on the container are relatively low, even when the force applied by the plunger to the stopper is relatively high. In these ways, the injection device can be used for the injection of medicaments of relatively high viscosity without affecting device reliability or patient comfort.

The drive means preferably comprises a drive spring arranged to apply a rotational force to the driveshaft. The drive spring may be housed in the drive body. In a particularly preferred embodiment, the drive spring comprises a spiral-wound spring, such as a power spring. Advantageously, when a power spring or spiral-wound spring is used, the axial dimension of the spring can be relatively short compared to an equivalent compression spring or other linear-acting spring, so that the device can be relatively compact. An outer end of the spring may be anchored to the drive body and an inner end of the spring may be anchored to the driveshaft.

The drive body is preferably arranged for axial movement with respect to the housing. For example, the drive body may be axially movable with respect to the housing from a first position to a second position. By allowing for axial movement of the drive body with respect to the housing, the length of the components of the stopper drive arrangement, in particular the plunger, can be minimised, to help reduce flexing or deformation of those components as force is transferred from the drive means to the stopper during operation of the stopper drive arrangement. The device may comprise a carrier arranged to receive the container, and the carrier may be moveable with respect to the housing. Preferably, movement of the drive body causes movement of the carrier.

The starting position of the container may be a retracted position in which the needle is retracted in the housing. In this way, the needle may be shrouded by the housing. When in the insertion position, the needle may project from a distal end of the housing. The advancing mechanism may control the axial movement of the drive body. In one embodiment, the advancing mechanism comprises biasing means arranged to bias the drive body for axial movement with respect to the housing. The biasing means may comprise a compression spring.

The advancing mechanism may be arranged to move the drive body from the first position to the second position, thereby to cause movement of the container from the starting position to the insertion position. For example, the advancing mechanism may be arranged to latch the drive body in the first position, and to release the drive body to move to the second position. The advancing mechanism may be arranged to engage with the plunger to latch the drive body in the first position, and to disengage from the plunger to release the drive body to move to the second position. In one embodiment, the advancing mechanism comprises at least one latching member for engagement with the plunger and a trigger component, such as a trigger button, that is moveable to disengage the latching member from the plunger.

Preferably, axial movement of the drive body to an activation position triggers activation of the stopper drive arrangement. In this way, delivery of the medicament starts automatically once the drive body has moved to the activation position. The activation position may be the second position.

The device may further comprise a clutch member moveable with respect to the drive body between a locked position in which the clutch member blocks rotation of the driveshaft and an unlocked position in which the driveshaft can rotate. Axial movement of the drive body to the activation position may cause relative movement of the clutch member from the locked position to the unlocked position.

To allow for automatic release of the clutch member upon axial movement of the drive body, the clutch member may be axially movable with the drive body and relative to the housing to a stop position, and further axial movement of the drive body relative to the housing to the activation position may cause movement of the clutch member with respect to the drive body to the unlocked position. A stop may be provided for blocking further axial movement of the clutch member when the clutch member reaches the stop position.

The clutch member may comprise a coupling member arranged to engage with the drive body to hold the clutch member in the locked position and to disengage from the drive body to allow the clutch member to move to the unlocked position. A control member may be arranged to prevent disengagement of the coupling member from the drive body until the clutch member reaches the stop position. The coupling member may move radially with respect to the drive body to disengage from the drive body.

The drive body may comprise a recess for receiving a head part of the coupling member to engage the coupling member with the drive body, in which case the control member may prevent movement of the head part out of the recess until the clutch member reaches the stop position. The head part and/or the recess may comprise a ramp formation to bias the head part out of the recess upon relative movement of the drive body and the clutch member. The control member may comprise a control surface for engagement with the coupling member and a recess on a distal side of the control surface for receiving the coupling member when the clutch member reaches the stop position.

The driveshaft may be provided with a clutch plate, and the clutch member may be arranged to engage with the clutch plate when the clutch member is in the locked position and to disengage from the clutch plate when the clutch member is in the unlocked position. For example, the clutch member may comprise at least one engagement pin for engagement with the clutch plate. The clutch plate may include at least one recess for receiving the engagement pin. When the clutch member is in the locked position, the engagement pins may extend through the drive body.

In some configurations, the stopper drive arrangement of the injection devices of the first aspect of the invention provides a self-contained, compact drive unit for driving a plunger in an injection device with high force, and may be used in other injection devices.

Accordingly, in a second aspect, the present invention extends to an injection device for the delivery of a medicament from a container through a needle disposed at the distal end of the container, the container having a stopper for containing the medicament within the container, the device comprising a housing for receiving the container, a drive body, a driveshaft arranged for rotation with respect to the drive body, a plunger arranged for axial movement with respect to the drive body to move the stopper towards the distal end of the container upon rotation of the driveshaft, drive means arranged to apply a rotational force to the driveshaft, a clutch member moveable with respect to the drive body between a locked position in which the clutch member blocks rotation of the driveshaft and an unlocked position in which the driveshaft can rotate, a coupling member arranged to engage with the drive body to hold the clutch member in the locked position and to disengage from the drive body to allow the clutch member to move to the unlocked position, and a control member cooperable with the coupling member to prevent disengagement of the coupling member from the drive body when the drive body is in a first position relative to the control member and to release the coupling member to disengage from the drive body when the drive body is in a second position relative to the control member.

The coupling member may be attached to the clutch member. The drive body may comprise a recess for receiving a head part of the coupling member to engage the coupling member with the drive body, and the control member may prevent movement of the head part out of the recess when the drive body is in the first position relative to the control member. The head part may be biased to move out of the recess when the drive body is in the second position relative to the control member, for example as a result of relative movement between the drive body and the clutch member.

The control member may comprise a control surface for engagement with the coupling member when the drive body is in the first position relative to the control member and a recess adjacent to the control surface for receiving the coupling member when the drive body is in the second position relative to the control member.

Movement of the clutch member from the locked position to the unlocked position may be axial with respect to the drive body, and the coupling member may move radially with respect to the drive body to disengage from the drive body. The control member may be fixed with respect to the housing, and the drive body may be movable with respect to the housing. In this way, movement of the drive body relative to the housing results in movement of the plunger relative to the drive body to drive the stopper of the container.

The driveshaft may be provided with a clutch plate, and the clutch member may be arranged to engage with the clutch plate when the clutch member is in the locked position and to disengage from the clutch plate when the clutch member is in the unlocked position.

Preferred and/or optional features of the first aspect of the invention may also be used, alone or in appropriate combination, in the second aspect of the invention.

Embodiments of the present invention will now be described, by way of example only, with reference to the accompanying drawings, in which like reference numerals are used for like features, and in which.

Figure 1:
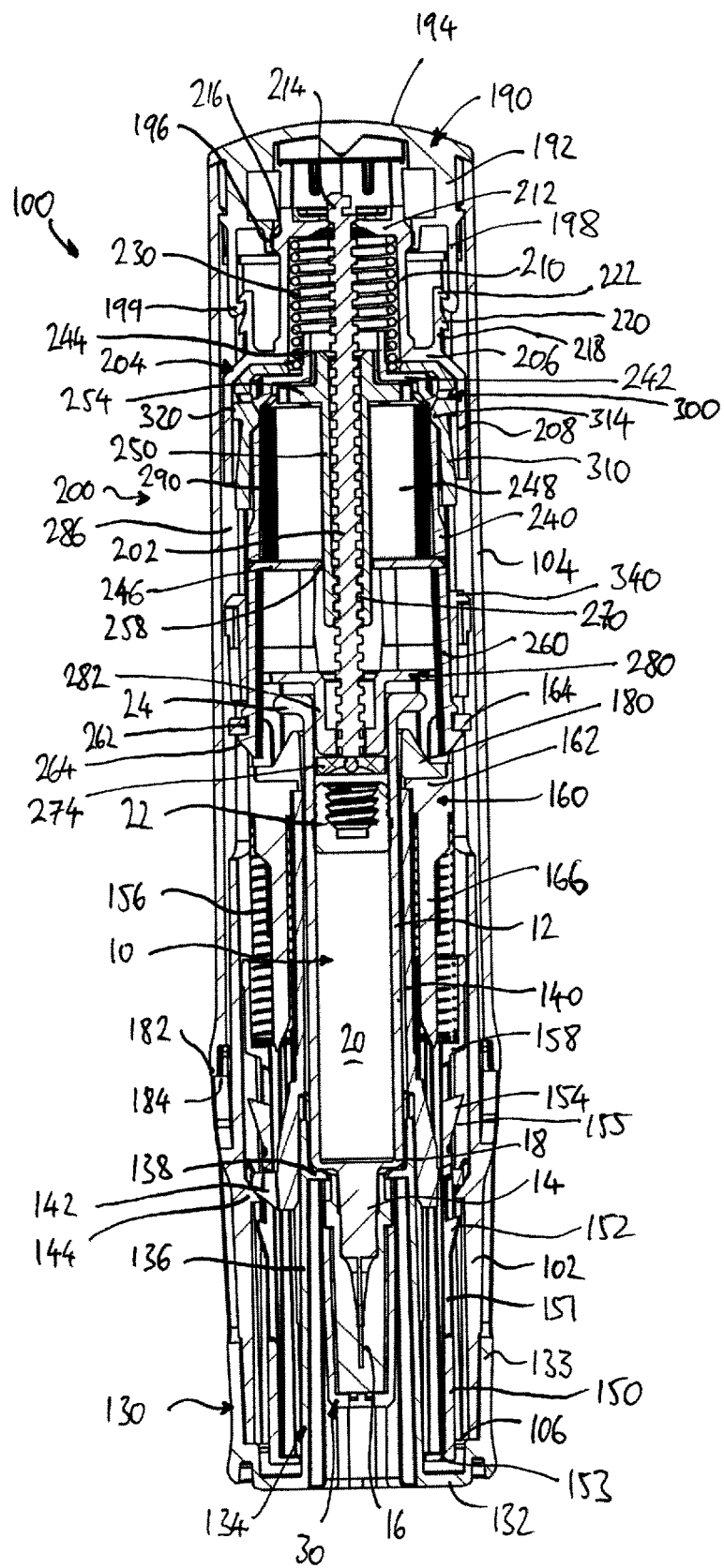
FIG. 1 is a cross-sectional view of an injection device according to the present invention in a first state.
Figure 3:
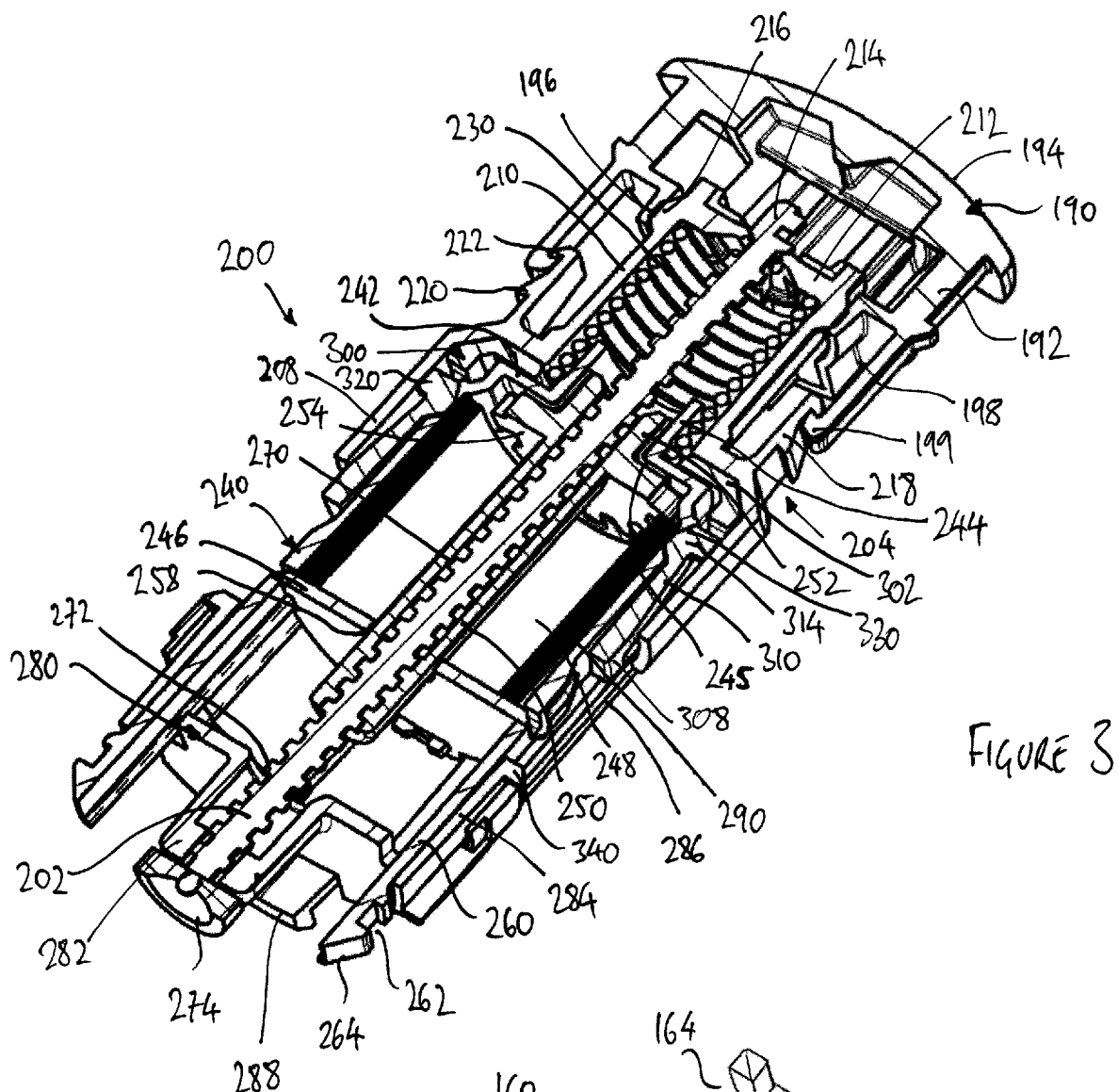
FIG. 3 is a cut-away isometric view of a drive assembly of the device of FIG. 1 in the first state.
Figure 2:
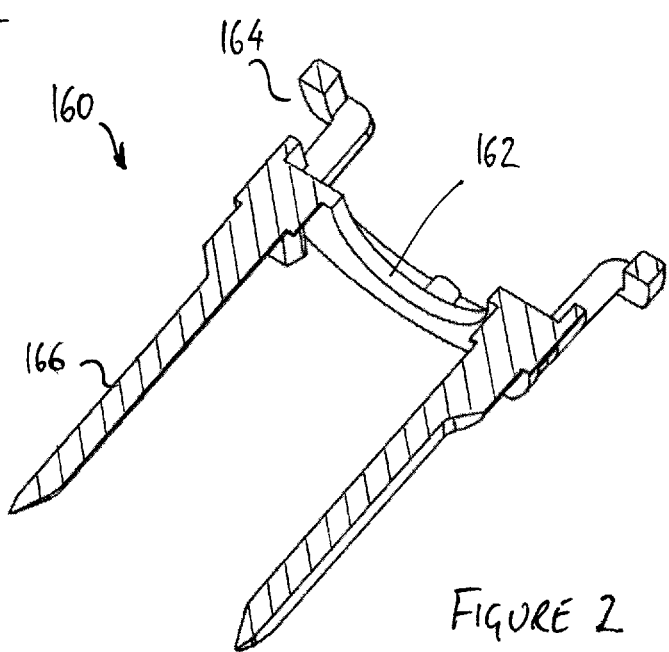
FIG. 2 is a cut-away isometric view of a spring guide component of the device of FIG. 1.
Figure 5:
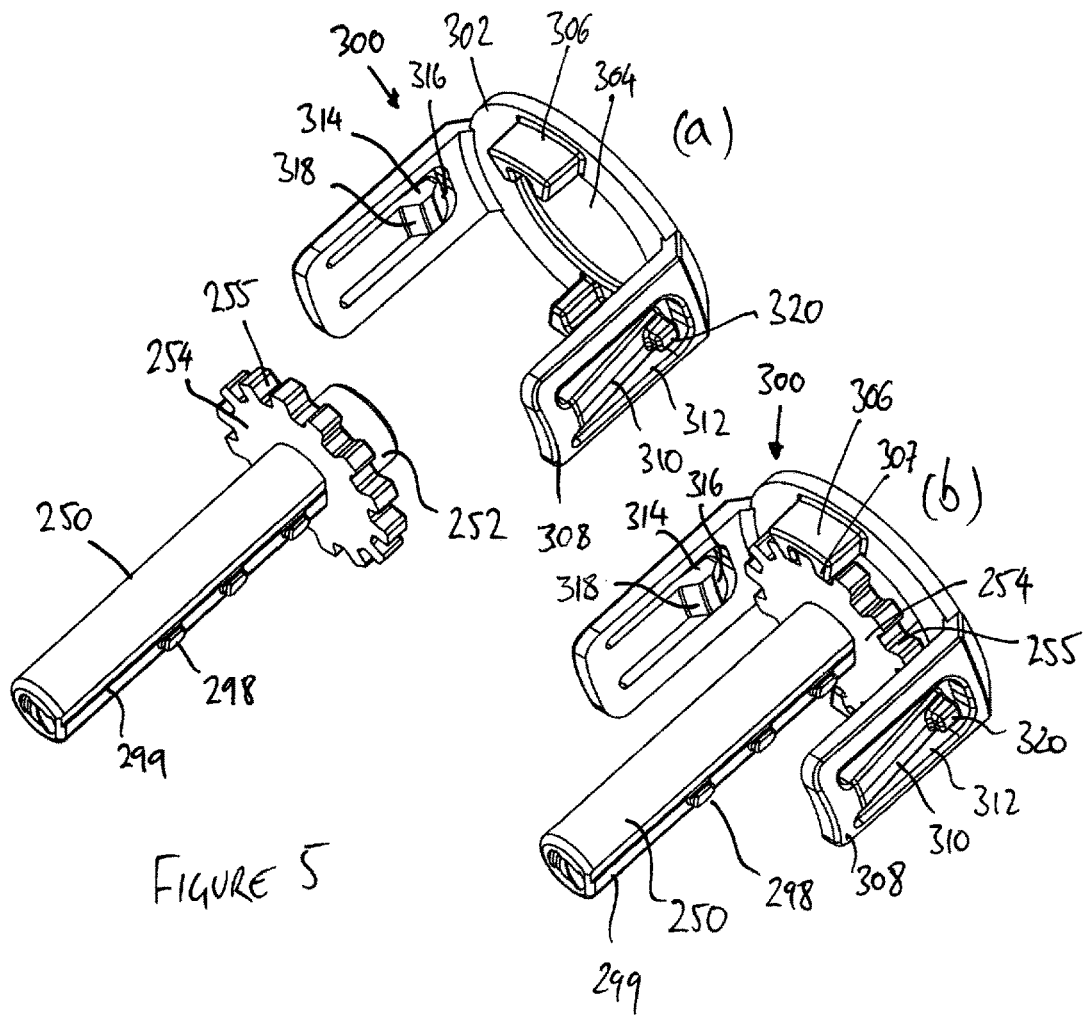
Figure 6:
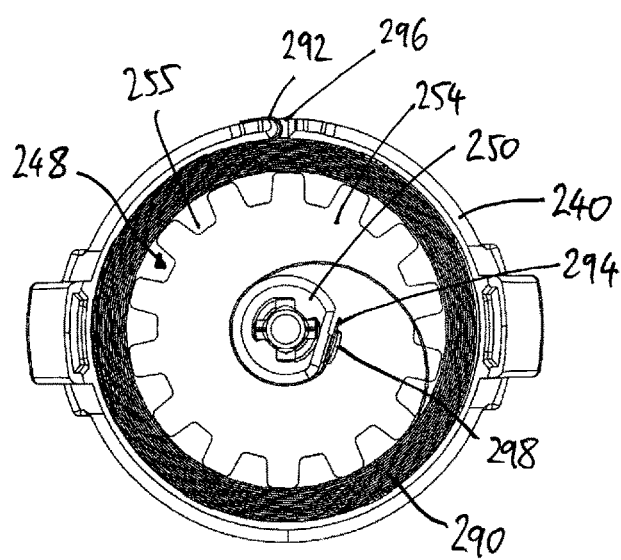
Figure 11:
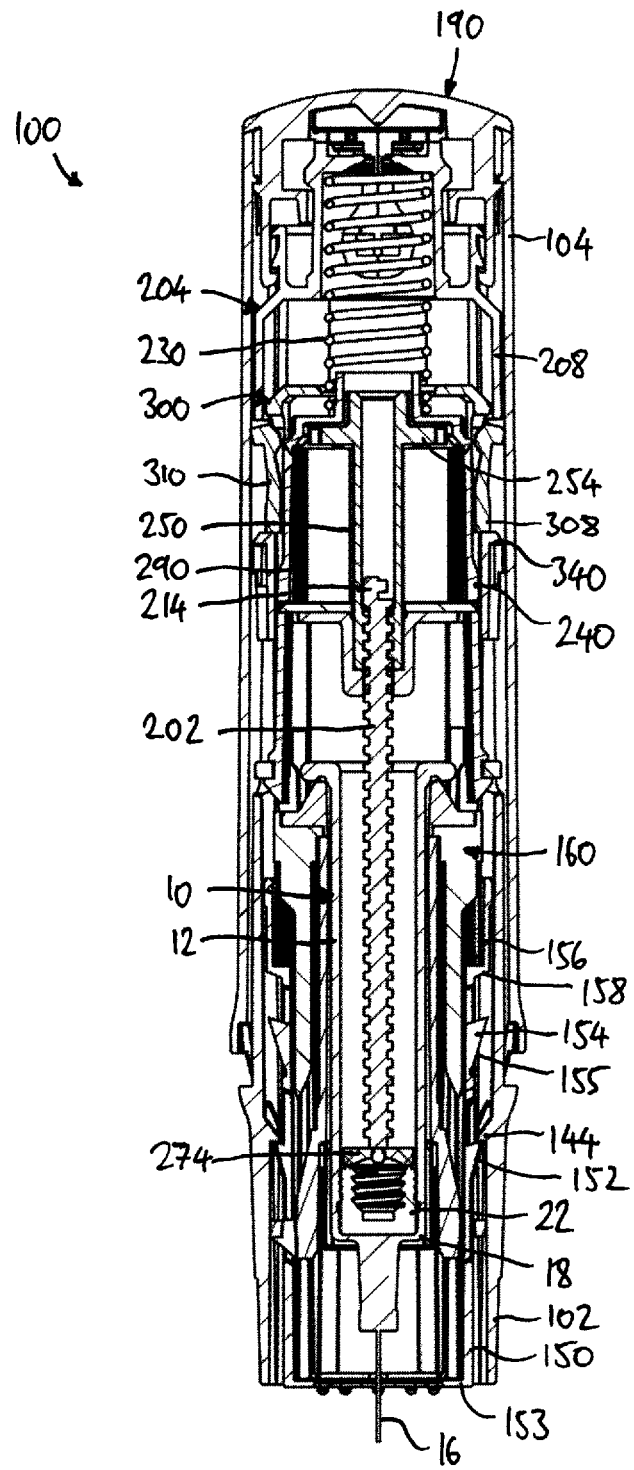
Figure 12:
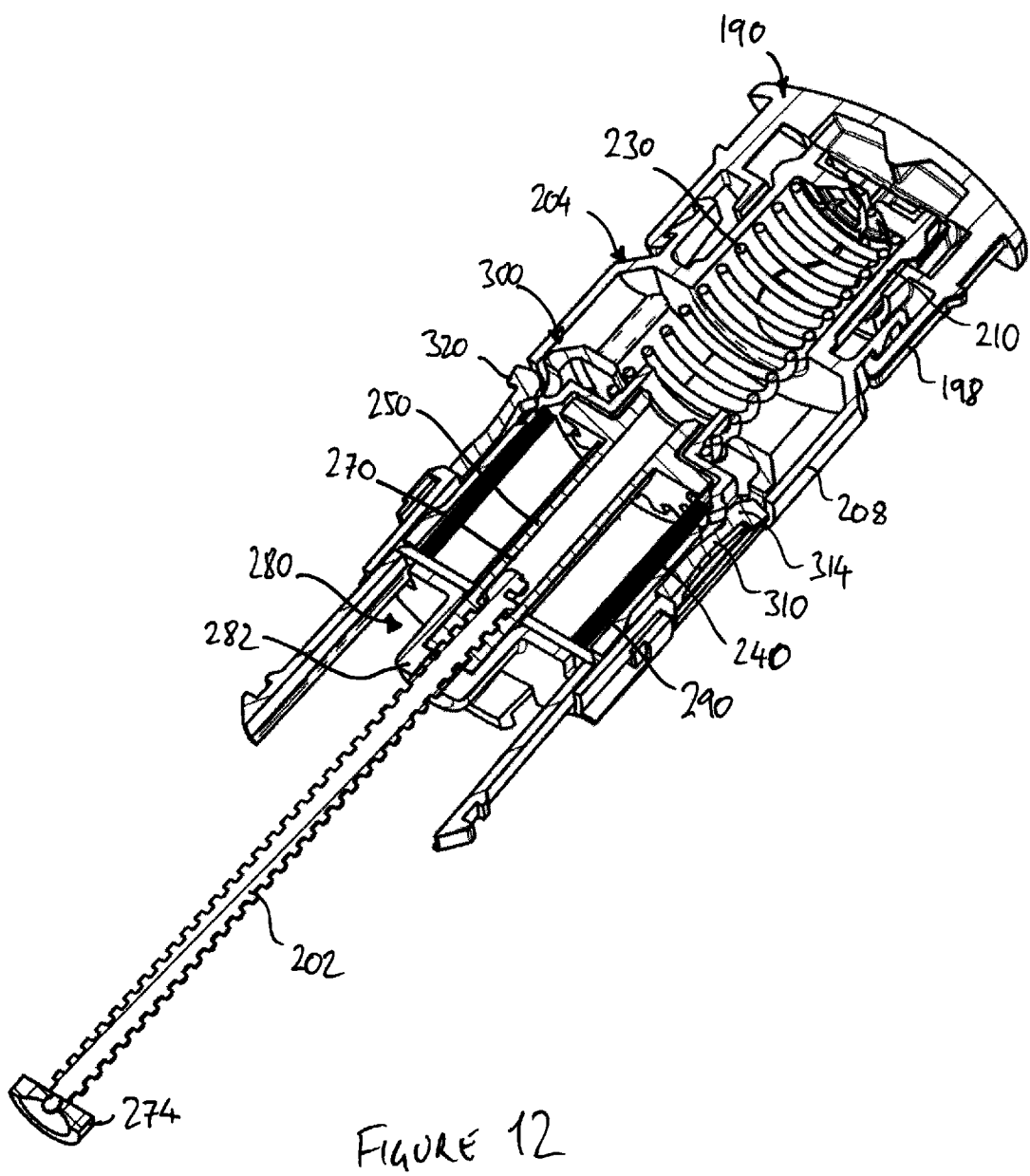

FIGS. 4(a) and 4(b) are assembled and exploded isometric views, respectively, of a power unit of the drive assembly of FIG. 3;

FIGS. 5(a) and 5(b) are exploded and assembled isometric views, respectively, of a clutch assembly of the power unit of FIGS. 4(a) and 4(b);

FIG. 6 is an internal view of the power unit of FIGS. 4(a) and 4(b);

FIG. 7(a) is a cross-sectional view showing the injector of FIG. 1 in a second state, and FIG. 7(b) shows part of FIG. 7(a) on an enlarged scale;

FIG. 8(a) is a cut-away isometric view showing the drive assembly of FIG. 3 in the second state, and FIG. 8(b) shows part of FIG. 8(a) on an enlarged scale;

FIG. 9(a) is a cross-sectional view showing the injector of FIG. 1 in a third state, and FIG. 9(b) shows part of FIG. 9(a) on an enlarged scale;

FIG. 10(a) is a cut-away isometric view showing the drive assembly of FIG. 3 in the third state, and FIG. 10(b) shows part of FIG. 10(a) on an enlarged scale;

FIG. 11 is a cross-sectional view showing the injector of FIG. 1 in a fourth state; and FIG. 12 is a cut-away isometric view showing the drive assembly of FIG. 3 in the fourth state.

Throughout the following description, the terms "front", "distal" and related terms are used to refer to the end of the device that is towards the patient's skin in use (i.e. the lower end of the device in FIG. 1), and the terms "rear", "proximal" and related terms are used to refer to the end of the device that is furthest from the skin in use (i.e. the upper end of the device in FIG. 1). Terms such as "turning" and "rotation" are intended to describe turning movement around the longitudinal axis of the device (i.e. the vertical axis in FIG. 1), except if the context demands otherwise.

FIGS. 1 to 6 show an injection device 100 according to one embodiment of the invention while in a first, initial state.

Referring first to FIG. 1, the injection device 100 comprises a housing having a front housing body 102 and a rear housing body 104. The front and rear housing bodies 102, 104 together contain a medicament container in the form of a pre-filled syringe 10.

The syringe 10 comprises a generally tubular glass body or barrel 12. At its distal end, the barrel 12 is formed into a reduced-diameter end portion 14 that carries a staked hypodermic needle 16. A shoulder 18 of the barrel 12 is formed where the end portion 14 meets the remaining portion of the barrel 12. The barrel 12 is filled with a quantity of medicament 20 and is closed by a stopper 22 that is slidably received in the barrel 12. An outwardly-projecting flange 24 is provided at the proximal end of the barrel 12. In the initial state of the device 100, a removable needle shield 30 is attached to the distal end portion 14 of the barrel 12, to seal the needle 16 and prevent leakage of the medicament 20 from the container. The syringe 10 may be of a type generally known in the art, for example as available under the registered trade mark Hypak (Becton Dickinson, N.J., USA).

The front housing body 102 is generally tubular to define an aperture 106 at its distal end. In the initial state of the device, the aperture 106 is closed by a removable cap 130. The cap 130 comprises a distal end face 132, a generally tubular outer wall 133, and a shield retainer 134 comprising a pair of retainer arms 136 that extend proximally from the end face 132 to embrace the needle shield 30 therebetween. Each retainer arm 136 is provided with an inwardly-directed engagement formation 138 that engages with a proximal end face of the needle shield 30, so that the needle shield 30 is retained by the cap 130 and removed from the syringe 10 when the cap 130 is removed from the front housing body 102.

The syringe barrel 12 is received in a generally tubular syringe carrier 140. The syringe carrier 140 is axially movable with respect to the front housing body 102, and the syringe barrel 12 is an interference fit in the syringe carrier 140 so that, in this example, movement of the syringe carrier 140 causes movement of the syringe 10.

The syringe carrier 140 is provided with a pair of ramped clips 142 (only one of which is shown in FIG. 1) that cooperate with ramped stops 144 provided on the front housing body 102 to prevent distal movement of the syringe carrier 140 with respect to the front housing body 102 when the device 100 is in its initial state.

A generally tubular shroud 150 is arranged concentrically between a distal part of the syringe carrier 140 and the front housing body 102. The shroud 150 includes longitudinally-extending slots 151 through which the clips 142 of the syringe carrier 140 extend to mate with the stops 144 of the front housing body 102. The shroud 150 is movable with respect to both the syringe carrier 140 and the front housing body 102, and is provided with a pair of stop formations 152 and a pair of latching clips 154 that are spaced proximally from the stop formations 152 and from the slots 151. As will be described in more detail below, the stop formations 152 and the latching clips 154 are both arranged to cooperate with the stops 144 of the front housing body 102 to control movement of the shroud 150 relative to the front housing body 102.

When the device 100 is in its initial state, as shown in FIG. 1, movement of the shroud 150 in the distal direction is prevented because the clips 142 of the syringe carrier 140 contact the proximal ends of the slots 151. In this position, the stops 144 of the front housing body 102 are in an intermediate position between the stop formations 152 and the latching clips 154.

The shroud 150 is biased in the distal direction by a pair of compression springs, referred to hereafter as lockout springs 156. The lockout springs 156 are arranged on either side of a proximal part of the syringe carrier 140, and are held in place by a spring guide 160, shown in more detail in FIG. 2. The spring guide 160 comprises an annular collar 162 and a pair of guide pins 166 that extend distally from the collar 162. A pair of arch formations 164 are provided on the proximal side of the collar 162.

Referring back to FIG. 1, each guide pin 166 carries one of the lockout springs 156, so that the proximal end of each lockout spring 156 acts against the collar 162 and the distal end of each lockout spring 156 acts against a shoulder 158 of the shroud 150. The distal end of the syringe carrier 140 contacts the proximal side of the collar.

A damping collar 180 encircles the syringe body 12 on the distal side of the flange 24. The damping collar 180 is of an elastomeric material such as natural or synthetic rubber. The damping collar 180 is shaped to extend between the syringe body 12 and the collar 162 of the spring guide 160, so that the damping collar 180 grips the syringe body 12 and holds the syringe in place relative to the spring guide 160 and the syringe carrier 140.

The rear housing body 104 is generally tubular, and a distal part of the rear housing body 104 is slidably fitted over a proximal part of the front housing body 102 in a concentric arrangement. The rear housing body 104 is axially displacable with respect to the front housing body 102. When the cap 130 is in place, the distal end 182 of the rear housing body 104 abuts the proximal end 184 of the outer wall 133 of the cap 130, so that movement of the rear housing body 104 with respect to the front housing body 102 is not possible while the cap 130 is in place.

A trigger button 190 is clipped to the proximal end of the rear housing body 104, so that the trigger button 190 and the rear housing body 104 are coupled for joint axial movement.

The rear housing body 104 houses a drive mechanism 200 of the device, which serves to control axial movement of the syringe 10 relative to the front housing body 102 for insertion of the needle 16 into the skin and to drive the stopper 22 of the syringe 10 for injection of the medicament 20.

The drive mechanism 200, which is shown in more detail in FIG. 3, includes an advancing mechanism and a stopper drive arrangement having a plunger 202. As will be explained in more detail below, the advancing mechanism is arranged to move the stopper drive arrangement in the distal direction relative to the front housing body 102 upon activation of the advancing mechanism, which causes insertion of the needle 16. This distal movement also activates the stopper drive arrangement to drive further movement of the plunger 202 in the distal direction with respect to the syringe body 12 to push the stopper 22 of the syringe 10.

The advancing mechanism includes a latch body 204 that includes a base part 206, a tubular sleeve part 208 that extends distally from the base part 206, and a pair of latch arms 210 that project proximally from the base part 206. Each latch arm 210 has an arcuate cross-section so that the latch arms 210 together have a generally tubular shape and are arranged concentrically around the plunger 202. The proximal ends of the latch arms 210 are provided with inwardly-projecting flanges 212 to engage with a head formation 214 of the plunger 202. A bearing ridge 216 is provided on the outer surface of each latch arm 210 adjacent to its proximal end.

The latch body 204 also includes a pair of retaining fingers 218 that extend proximally from the base part 206. The retaining fingers 218 are arranged parallel to and spaced outwardly from the latch arms 210. Each retaining finger 218 includes a distal clip formation 220 and a proximal clip formation 222.

The trigger button 190 comprises a button chassis 192 that carries a proximal button face 194 and an internal annular holding ring 196 that is spaced distally from the button face 194. A pair of arms 198 extend distally from the button chassis 192 to engage with the retaining fingers 218 of the latch body 204.

When the device is in its initial state, as shown in FIGS. 1 and 3, a hook formation 199 at the end of each arm 198 of the button 190 hooks over the proximal clip formation 222 of the retaining finger 218 to prevent distal movement of the trigger button 190 with respect to the latch body 204.

With the trigger button 190 in this position, the holding ring 196 of the trigger button 190 bears against the bearing ridge 216 of each latch arm 210. In this way, the flanges 212 of the latch arms 210 are kept together, preventing the head formation 214 of the plunger 202 passing the flanges 212 and stopping the plunger 202 from moving distally with respect to the latch body 204.

An insertion spring 230 in the form of a compression spring is disposed around the plunger 202. A proximal end of the insertion spring 230 bears against the distal faces of the flanges 212 of the latch arms 210. The distal end of the insertion spring 230 acts against a drive body 240, which forms part of the stopper drive mechanism as will now be described.

Referring additionally to FIGS. 4(a), 4(b), 5(a) and 5(b), the drive body 240 is generally can-shaped, and is arranged concentrically around the plunger 202. The drive body 240 retains a driveshaft 250 which includes a journal 252 at its proximal end and a toothed gear or clutch plate 254 disposed on the distal side of the journal 252.

As shown most clearly in FIG. 3, a proximal end face 242 of the drive body 240 is provided with a tubular throat 244 for receiving the journal of the driveshaft 250. A flanged thrust washer 245 is inserted between the journal 252 and the throat 244 to reduce friction between the driveshaft 250 and the drive body 240. The insertion spring 230 is received concentrically around the throat 244 and bears upon the proximal end face 242 of the drive body 240.

An end plate 246 is clipped to the distal end of the drive body 240 to enclose a spring cavity 248 within the drive body 240. The driveshaft 250 extends through an aperture 258 in the end plate. A pair of connecting arms 260 extend distally from the drive body 240 to engage with the arches 164 of the spring guide 160. Each connecting arm 260 has a recess 262 adjacent to its distal end for receiving the respective arch 164, and a ramped formation 264 disposed on a distal side of the recess 262 to allow the arches 164 to snap into the recesses 262 during assembly of the device 100.

The driveshaft 250 includes a partially threaded bore 270 to receive the plunger 202. As shown most clearly in FIGS. 4(a) and 4(b), the plunger 202 is provided with four rows of studs 272 along its length, with the studs 272 being arranged in a helical configuration to engage with the threads of the bore 270. The distal end of the plunger 202 is provided with a disc-shaped foot 274 for engagement with the stopper 22 of the syringe.

The plunger 202 is supported at its distal end by a plunger guide component 280, shown most clearly in FIG. 3. The plunger 202 extends through a guide bush 282 of the plunger guide component. The guide bush 282 has a cross-shaped bore to match the four rows of studs 272 on the plunger 202, so that the plunger 202 can move axially with respect to the guide bush 282 but so that rotation of the plunger 202 with respect to the guide bush 282 is prevented.

The plunger guide component 280 also includes a proximal pair of clips 284 to attach the plunger guide component 280 to the latch body 204. To this end, the sleeve part 208 of the latch body 204 is provided with a pair of diametrically-opposed, elongate recesses or slots 286, and the proximal clips 284 engage with the distal ends of the slots 286. The plunger guide component 280 also includes a distal pair of clips 288 (only one of which is visible in FIG. 3) to attach the plunger guide component 280 to the front housing body 102 (not shown in FIG. 3). In this way, the plunger guide component 280 fixes the position of the latch body 204 with respect to the front housing body 102.

Referring additionally to FIG. 6, the spring cavity 248 of the drive body 240 houses a drive spring 290. The drive spring 290 comprises a spiral-wound strip of spring steel, known in the art as a power spring. The outer end 292 of the drive spring is anchored to the drive body 240, and the inner end 294 of the drive spring 290 is attached to the driveshaft 250.

The drive spring 290 can be attached to the drive body 240 and the driveshaft 250 in any suitable way. In the illustrated example, the wall of the drive body 240 has a longitudinally-extending slot 296, and the outer end 292 of the spring 290 is folded backwards into a hook form that hooks over the edge of the slot 296. The driveshaft 250 is provided with a plurality of mushroom-shaped nubs 298 that are arranged along a flat 299 of the driveshaft 250, and the inner end 294 of the drive spring 290 is provided with a corresponding number of holes to accept the nubs 298. The force applied by the drive spring 290 helps to keep the hook form in engagement with the drive body 240 and the periphery of each hole in engagement with the respective nub 298.

Referring back to FIGS. 1 and 3 to 5, the stopper drive mechanism includes a clutch component 300 arranged to prevent rotation of the driveshaft 250 under the influence of the drive spring 290 until the stopper drive mechanism is activated. As shown in FIGS. 4(a) and 4(b), the clutch component 300 comprises a base plate 302 having an aperture 304, a pair of distally-projecting engagement pins 306, and a pair of coupling arms 308 that extend distally from the base plate to embrace the drive body 240 therebetween.

With the device in its initial state, the clutch component 300 is in a locked position in which the base plate 302 of the clutch component 300 is positioned next to the proximal end face 242 of the drive body 240, with the throat 252 of the drive body 240 and the insertion spring 230 extending through the aperture 304. The engagement pins 306 extend through apertures (not shown) in the proximal end face 242 of the drive body 240. As seen most clearly in FIG. 5(b), which shows the clutch component 300 in the locked position with the drive body 240 omitted, the engagement pins 306 are shaped to cooperate with the toothed clutch plate 254 of the driveshaft 250 to block rotation of the driveshaft 250 with respect to the drive body 240. In this example, each engagement pin 306 is provided with a pair of teeth 307 to engage with a pair of adjacent recesses 255 between the teeth of the clutch plate 254.

The axial position of the clutch component 300 relative to the drive body 240 is controlled by a pair of elongate coupling fingers 310. The coupling fingers 310 are mounted in respective slots 312 formed in the coupling arms 308. Each coupling finger 310 is attached to the respective coupling arm 308 at the distal end of the respective slot 312, while the remainder of the coupling finger 310 is free so that the coupling member can bend or flex.

The proximal end of each coupling finger 310 includes a head part 314 that is enlarged to protrude radially inwards with respect to the inner surface of the remainder of the coupling finger 310. Each head part 314 is shaped to provide ramped faces 316, 318 on its proximal and distal sides. The outer surface of each coupling finger 310 is shaped so that the coupling finger 310 becomes progressively thinner towards the head part 314, to increase the flexibility of the coupling fingers 310. An outwardly-directed control boss 320 is provided at the proximal end of each coupling finger 310.

When the clutch component 300 is in its locked position, the head parts 314 of the coupling fingers 310 are received in recesses 330 provided in the outer surface of the drive body 240. Referring to FIG. 4(b), each recess has a complementary shape to the head part 314 of the respective coupling finger 310, and correspondingly includes ramped proximal and distal faces 332, 334.

Referring back to FIGS. 1 and 3, when the device 100 is in its initial state, the sleeve part 208 of the latch body 204 acts as a control member to keep the head parts 314 of the coupling fingers 310 in engagement with the recesses 330 in the drive body 240. The outermost surface of the control boss 320 of each coupling finger 310 bears against the inner surface of the sleeve part 208, so that the inner surface of the sleeve part 208 acts as a control surface for the coupling fingers 310.

In the accompanying figures, the drive spring 290 is illustrated in an unwound state for clarity. However, in the initial state of the device 100, the drive spring 290 would be in a wound state. During assembly of the device 100, the driveshaft 250 would be rotated relative to the drive body 240 to wind the coils of the drive spring 290 onto the driveshaft 250 (e.g. by turning the driveshaft 250 anticlockwise in FIG. 6). The clutch component would then be engaged with the clutch plate of the driveshaft 250 to prevent clockwise rotation of the driveshaft 250 under the rotational force now applied by the drive spring 290.

Operation of the device 100 will now be described. The device 100 is supplied to a user in its initial state as shown in FIG. 1 (with the drive spring in its wound state, as described above). The clutch component 300 is held in its locked position with respect to the drive body 240. This prevents movement of the plunger 202 relative to the drive body 240. In turn, the drive body 240 is latched in a first position relative to the front housing body 102 by engagement of the latch arms 210 with the plunger 202. The cap 130 is fitted to the front housing body 102 to prevent movement of the rear housing body 104 and the trigger button 190 with respect to the front housing body 102, and to protect the needle 16 of the syringe. With the cap 130 in place, the front housing body 102 is not accessible to the user.

To prepare the device for use, the user grips the rear housing body 104 and pulls the cap 130 in the distal direction to remove the cap 130 and to unlock the rear housing body 104 for relative movement with respect to the front housing body 102. As the cap 130 is removed, the shield retainer 134 pulls the cap 130 off the front housing body 102 to expose the front housing body 102. Removal of the cap 130 may also pull the syringe 10 in the distal direction with respect to the syringe carrier, so that the flange 24 of the syringe 10 contacts the damping collar 180. The syringe 10 remains in a retracted position, with the distal end of the needle 16 located proximally with respect to the distal end of the front housing body 102.

After removal of the cap 130, the distal end of the device 100 is placed against the injection site, so that the distal end 153 of the shroud 150 contacts the skin. The shroud 150 moves proximally with respect to the front housing body 102, against the biasing force of the lockout springs 156, until the stop members 152 of the shroud 150 meet the stops 144 of the front housing body 102 to prevent further proximal movement of the shroud 150.

The advancing mechanism of the device 100 can then be activated by moving the trigger button 190, together with the rear housing body 104, in the distal direction relative to the front housing body 102. Upon distal movement of the trigger button 190, the holding surface 196 of the trigger button 190 moves distally away from the bearing ridges 216 of the latch arms 210. This allows the latch arms 210 to splay apart, releasing the head portion 214 of the plunger 202 to pass the flanges 212 of the latch arms 210. Although not shown in the accompanying drawings, the trigger button 190 may include ribs, pins or other formations that are arranged to force the latch arms 210 apart to release the plunger 202 upon distal movement of the trigger button 190. Distal movement of the trigger button 190 also causes the hook formations 199 at the end of the distally-extending arms 198 of the trigger button 190 to engage with the distal clip formations 220 of the retaining fingers 218 of the latch body 204, so as to lock the trigger button 190 to the latch body 204.

With the head of the plunger 202 released from the latch arms 210, the plunger 202 moves distally with respect to the latch body 204. The clutch component 300 remains in its locked position relative to the drive body 240, which prevents distal movement of the plunger 202 with respect to the drive body 240. Accordingly, the drive body 240 moves distally with the plunger 202. Because of the engagement between the connecting arms 260 of the drive body 240 and the arches 164 of the spring guide 160, the spring guide 160 and the syringe carrier 140 are also moved in the distal direction. This causes the clips 142 of the syringe carrier 140 to move past the stops 144 of the front housing body 102. The syringe carrier 140 carries the syringe 10 distally with respect to the front housing body 102 to advance the needle 16 through the aperture 106 in the distal end of the front housing body 102 and beyond the distal end 153 of the shroud 150 to pierce the skin at the injection site.

Distal movement of the drive body 240 causes the control bosses 320 of the coupling fingers 310 of the clutch component 300 to slide along the control surface provided by the sleeve part 208 of the latch member 204, keeping the head portion 314 of each coupling finger 310 in engagement with the respective recess 330 in the drive body 240. In this way, the clutch component 300 initially moves with the drive body 240 to remain in its locked position with respect to the drive body 240.

Figure 7:
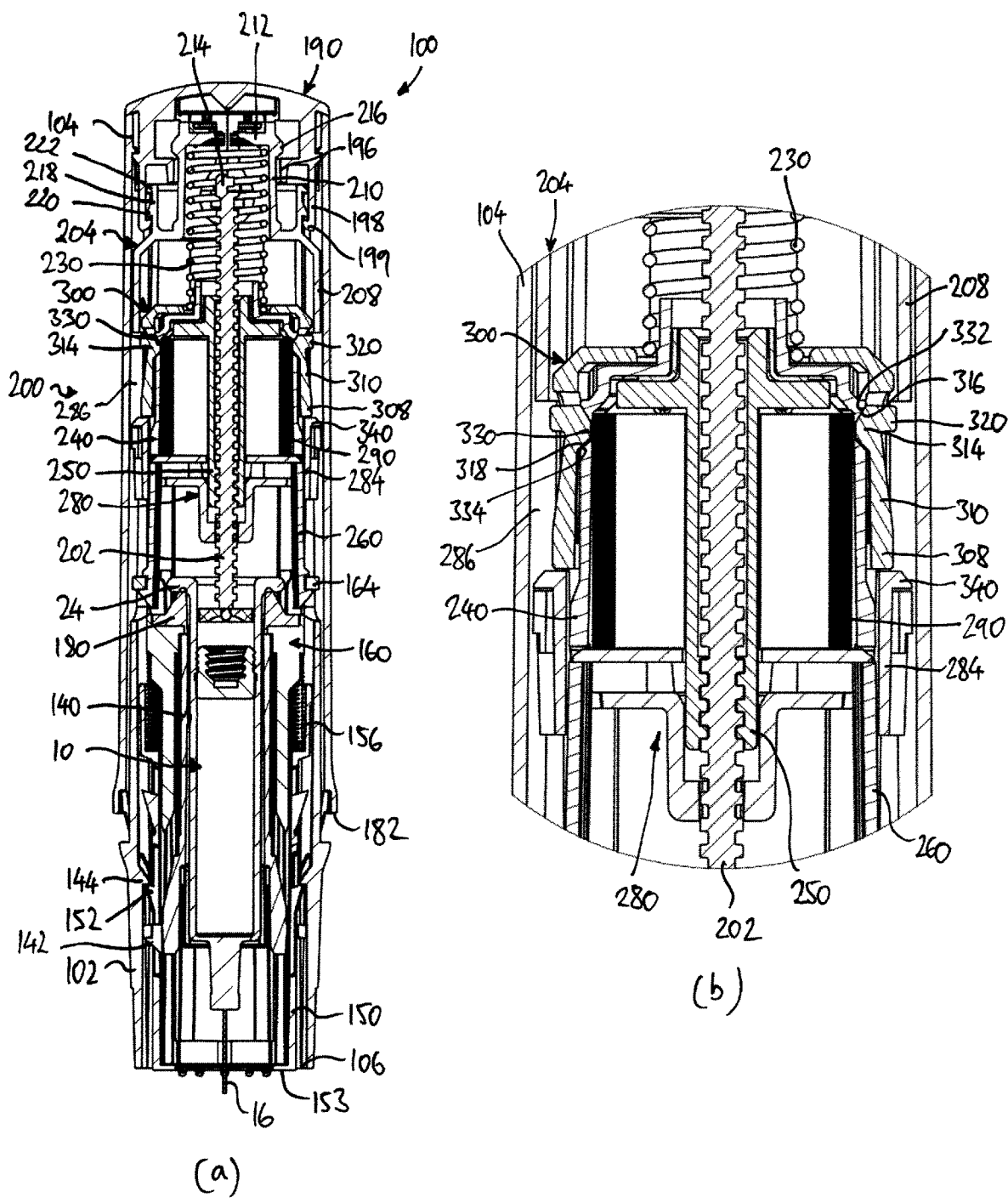
Figure 8:
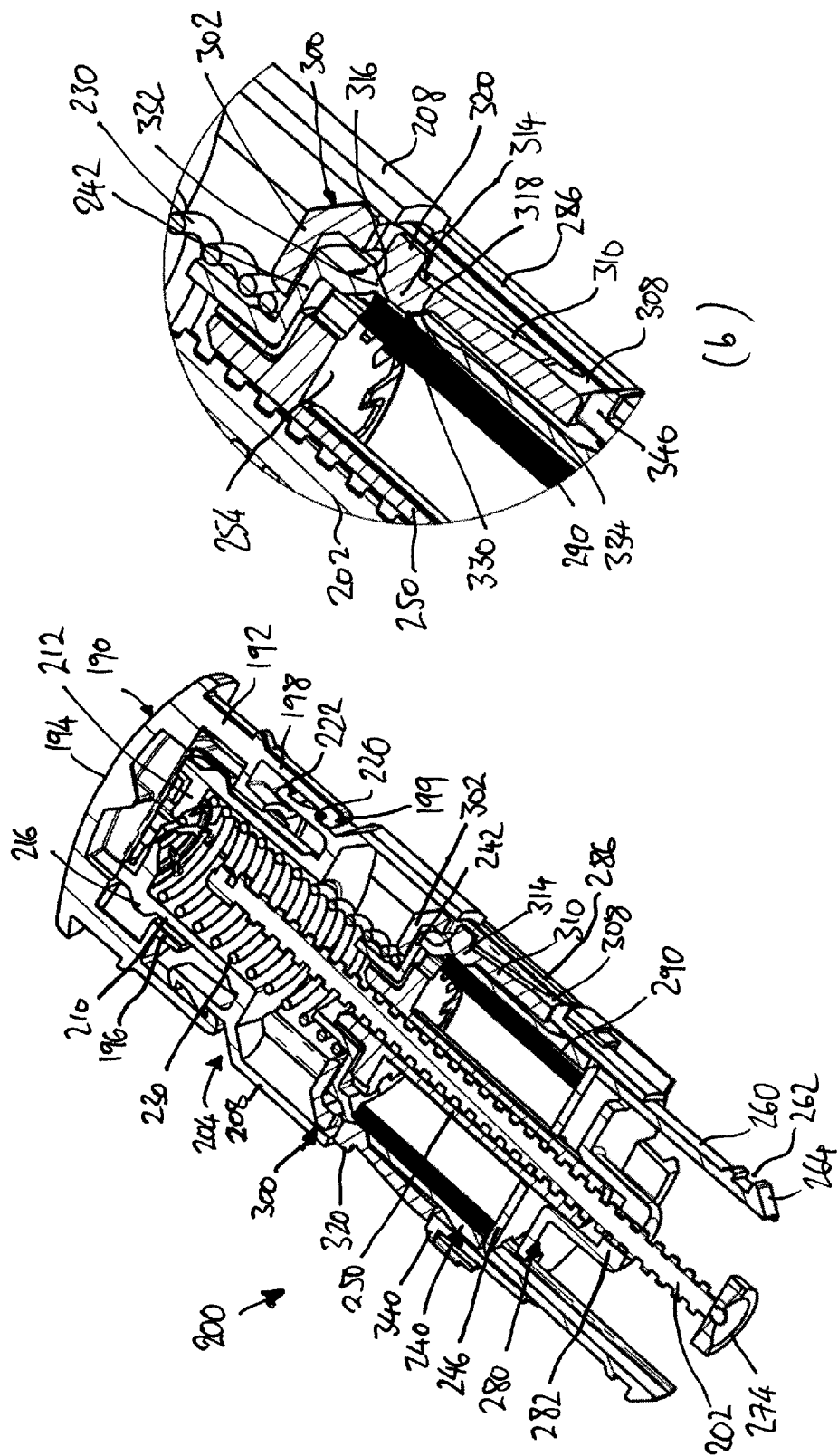

Joint distal movement of the clutch component 300 and the drive body 240 continues until the clutch component 300 reaches a stop position, in which the distal ends of each of the coupling arms 308 come into contact with a respective stop member 340. The stop members 340 are in a fixed position relative to the latch body 204 and, in this example, are defined by the end faces of the proximal clips 284 of the plunger guide component 280. FIGS. 7 and 8 show the device 100 and the drive mechanism 200 respectively when the clutch component 300 has just reached the stop position.

As shown most clearly in FIGS. 7(b) and 8(b), when the clutch component 300 moves into the stop position, the control boss 320 of each coupling finger 310 comes into register with the respective slot 286 in the sleeve part 208 of the latch body 204. Accordingly, the control surface no longer bears against the control boss 320, so that the coupling fingers 310 are free to flex outwardly.

The drive body 240 continues to move in the distal direction relative to the latch body 204 once the clutch component 300 has reached the stop position, but the stop members 340 prevent further distal movement of the clutch component 300 relative to the latch body 204. Accordingly, the drive body 240 now moves distally relative to the clutch component 300, and the interaction between the ramped face 316 on the proximal side of the head part 314 of each coupling finger 310 and the ramped proximal face 332 of the corresponding recess 330 biases the head part 314 of the respective finger 310 to move radially out of the recess 330.

Figure 9:
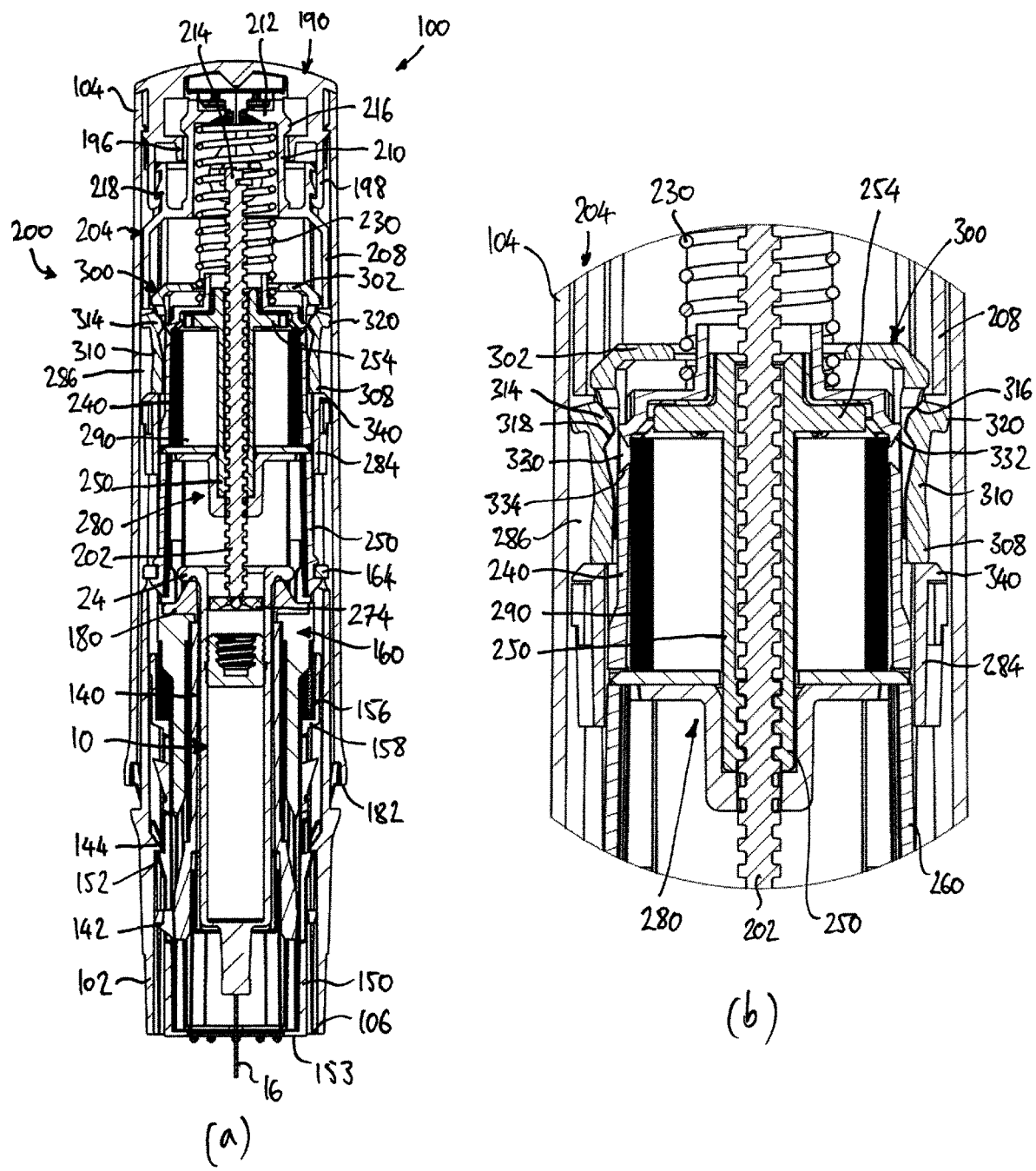
Figure 10:
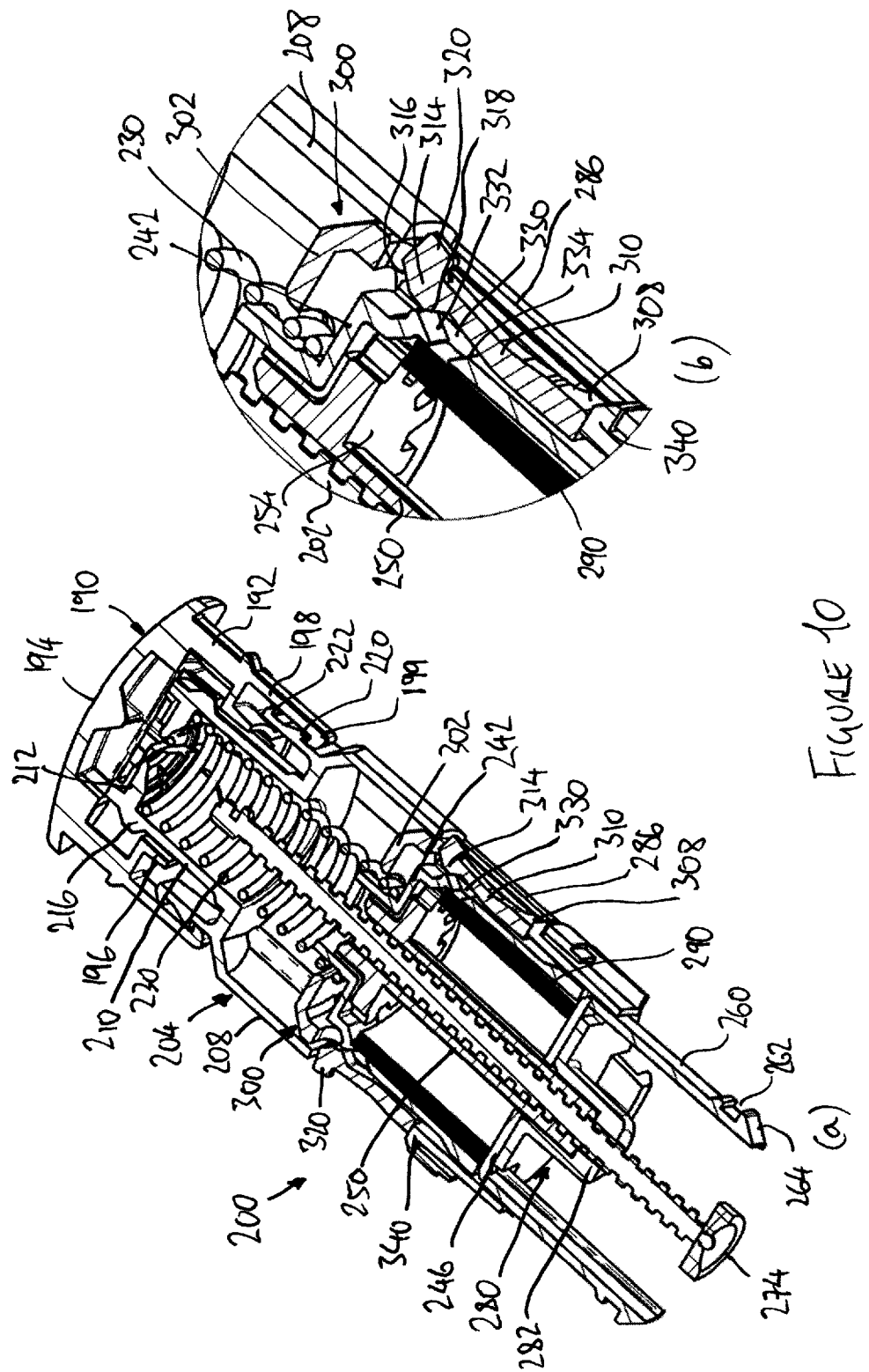

Movement of the drive body 240 continues until the drive body 240 reaches a second or activation position. FIGS. 9 and 10 show the device 100 and the drive mechanism 200, respectively, when the drive body 240 is in the activation position. In this state, further distal movement of the drive body 240 with respect to the front housing body 102 is prevented by contact between a guide member (not shown) provided on the syringe carrier 140 and a distal end surface of a guide channel (not shown) provided in the front housing body 102. Accordingly, the syringe carrier 140 now holds the syringe in an insertion position, with the needle 16 projecting beyond the distal end face 153 of the shroud 150 by a distance that corresponds to a required injection depth.

As shown most clearly in FIGS. 9(b) and 10(b), the coupling fingers 310 of the clutch component 300 have splayed outwardly into the slots 286 in the sleeve part 208 of the latch body 204, and the base plate 302 of the clutch component 300 and the drive body 240 are spaced apart so that the clutch component 300 is now in its unlocked position with respect to the drive body 240. In this state, the engagement pins 306 (not visible in FIGS. 9 and 10) no longer engage with the drive plate 254 of the driveshaft 250.

The driveshaft 250 is therefore able to rotate with respect to the drive body 240, under the rotational driving force applied by the drive spring 290. With the drive body 240, the plunger guide component 280, the spring guide 160, the syringe carrier 140 and the syringe 10 all now fixed in position with respect to the front housing body 102, rotation of the driveshaft 250 drives the plunger 202 to move distally, so as to bring the foot 274 of the plunger 202 into contact with the stopper 22 of the syringe. As rotation of the driveshaft 250 continues, the plunger 202 forces the stopper 22 of the syringe in the distal direction to expel medicament through the needle 16.

FIGS. 11 and 12 show the device 100 and the drive mechanism 200, respectively, at the end of an injection, when the stopper 22 has been pushed into contact with the shoulder 18 of the syringe body 12.

The device 100 can then be moved proximally from the injection site, to withdraw the needle 16 from the skin. The shroud 150 is biased to move in the distal direction by the lockout springs 156, so that the distal end face 153 of the shroud 150 remains in contact with the skin until the needle 16 has been fully withdrawn. In this way, the shroud 150 conceals the needle 16 from view as the needle 16 is withdrawn.

The shroud 150 moves distally with respect to the front housing body 102 until the latching clips 154 of the shroud 150 pass the stops 144 of the front housing body 102. The latching clips 154 have a ramped distal face 155 to cooperate with the stops 144, and the force applied to the shroud 150 by the lockout springs 156 is sufficient to cause the latching clips 154 to flex inwardly to pass the stops 144. The latching clips 154 then spring back outwardly, and the proximal faces of the latching clips 154 are shaped to prevent subsequent movement of the shroud 150 in the proximal direction. In this way, the shroud 150 becomes locked with its distal end face 153 disposed beyond the distal end of the needle 16, so that the needle 16 remains concealed and protected by the shroud 150 after use of the device 100.

It will be understood that, in the above-described embodiment, the characteristics of the insertion spring 230 and the drive spring 290 can be independently selected to optimise the performance of the device 100 for any particular application. In particular, the insertion spring 230 can be selected to provide a relatively low impact force to reduce the risk of damage to the device 100 and for patient comfort during needle insertion, whilst the drive spring 290 can be selected according to the viscosity of the medicament 20 and the dimensions of the needle 16.

Furthermore, the number of coils of the drive spring 290 can be selected so that, when the stopper drive arrangement is activated, the driveshaft 250 is driven to rotate by the number of turns required to drive the stopper 22 of the syringe 10 to its end position. The pitch of the internal thread of the driveshaft 250 will determine the distance moved by the plunger 202 per rotation.

It will be appreciated that several modifications and variations of the above-described embodiment of the invention are possible.

For example, the arrangement of the clutch component could differ from that described above. The clutch member may be biased into its locked position by a suitable biasing means, such as a compression spring provided between the clutch component and the latch body, so that the clutch member remains in its locked position until it reaches the stop position. In the case, the coupling fingers could be omitted.

In another arrangement, the teeth of the clutch plate and the engagement pins of the clutch component can be shaped to bias the clutch component in the distal direction with respect to the drive body under the influence of the rotational force applied by the drive spring. In this case, when the coupling fingers move into register with the recesses in the sleeve part of the latch member, cooperation between the teeth and the pins moves the clutch member into its unlocked position. In this case, the stop member could be omitted.

In the above-described example, the foot of the plunger does not contact the stopper of the syringe until the stopper drive arrangement has been activated, once the syringe has moved into the insertion position. However, it is also possible that the foot of the plunger could contact the stopper of the syringe during distal movement of the drive body before activation of the stopper drive arrangement. In this case, the action of the plunger on the stopper would assist in moving the syringe to the insertion position.

Different arrangements for transferring rotational movement of the driveshaft to linear movement of the plunger are also possible. For instance, the driveshaft could be externally threaded and the plunger could have an internally threaded bore to receive the driveshaft.

The power spring may be of any suitale type, and may be a constant-force spring or a variable-force spring. Instead of a power spring, any suitable type of spring could be used to drive rotation of the driveshaft. For example, the drive spring could be a torsion spring, such as a helical torsion spring. Any suitable way of anchoring the spring to the driveshaft and the drive body could be used.

The advancing mechanism could differ from that described above, and several suitable alternative mechanisms will be familiar to those skilled in the art. In the above-described embodiment, the advancing mechanism cooperates with the plunger to latch the drive body in the first position, but it will be appreciated that the advancing mechanism could instead cooperate with the drive body or with another component of the stopper drive arrangement to control its movement. Instead of a spring-driven advancing mechanism, the advancing mechanism could rely on a user-applied force to deploy the needle. Aspects of the present invention are not limited to single use, disposable devices such as that described above. With appropriate modification to allow resetting of the advancing mechanism and the stopper drive arrangement, aspects of the invention could be applied to re-usable devices, such as cartridge-type injectors. It would also be possible to adapt the stopper drive arrangement of the present invention for use in a device arranged for manual needle insertion, in which no advancing mechanism is provided.

Further modifications and variations of the examples described above are also possible without departing from the scope of the invention as defined in the appended claims.

The invention claimed is:

1. An injection device for delivery of a medicament from a container through a needle disposed at a distal end of the container, the container having a stopper for containing the medicament within the container, the device comprising:
   a housing;
   an advancing mechanism comprising a compression spring operable to move the container relative to the housing from a starting position in which the needle is shrouded and an insertion position in which the needle is exposed; and
   a stopper drive arrangement operable to move the stopper towards the distal end of the container, the stopper drive arrangement comprising:
      a drive body arranged for axial movement with respect to the housing;
      a driveshaft arranged for rotation with respect to the drive body;
      a plunger arranged for axial movement with respect to the drive body to move the stopper upon rotation of the driveshaft; and
      a drive spring arranged to rotate the driveshaft upon activation of the stopper drive arrangement,
      the drive spring being housed within the drive body.

2. The injection device according to claim 1, wherein the drive spring comprises a spiral-wound spring.

3. The injection device according to claim 2, wherein an outer end of the drive spring is anchored to the drive body and an inner end of the drive spring is anchored to the driveshaft.

4. The injection device according to claim 1, wherein the drive body is axially movable with respect to the housing from a first position to a second position.

5. The injection device according to claim 4, comprising a carrier arranged to receive the container and being moveable with respect to the housing, and wherein axial movement of the drive body causes movement of the carrier.

6. The injection device according to claim 4, wherein the compression spring is arranged to bias the drive body for axial movement with respect to the housing.

7. The injection device according to claim 4, wherein the advancing mechanism is arranged to move the drive body from the first position to the second position, thereby to cause movement of the container from the starting position to the insertion position.

8. The injection device according to claim 7, wherein the advancing mechanism is arranged to engage with the plunger to latch the drive body in the first position, and to disengage from the plunger to release the drive body to move to the second position.

9. The injection device according to claim 8, wherein the advancing mechanism comprises at least one latching member for engagement with the plunger, and a trigger component moveable to disengage the at least one latching member from the plunger.

10. The injection device according to claim 4, wherein axial movement of the drive body to an activation position triggers activation of the stopper drive arrangement.

11. The injection device according to claim 10, wherein the activation position is the second position.

12. The injection device according to claim 10, further comprising a clutch moveable with respect to the drive body between a locked position in which the clutch blocks rotation of the driveshaft and an unlocked position in which the driveshaft can rotate, and wherein axial movement of the drive body to the activation position causes relative movement of the clutch from the locked position to the unlocked position.

13. The injection device according to claim 12, wherein the clutch is axially movable with the drive body and relative to the housing to a stop position, and wherein further axial movement of the drive body relative to the housing to the activation position causes movement of the clutch with respect to the drive body to the unlocked position.

14. The injection device according to claim 13, comprising a stop for blocking further axial movement of the clutch when the clutch reaches the stop position.

15. The injection device according to claim 13, wherein the clutch comprises a coupling member comprising coupling fingers arranged to engage with the drive body to hold the clutch in the locked position and to disengage from the drive body to allow the clutch to move to the unlocked position.

16. The injection device according to claim 15, further comprising a control member comprising a sleeve arranged to prevent disengagement of the coupling member from the drive body until the clutch reaches the stop position.

17. The injection device according to claim 16, wherein the coupling member moves radially with respect to the drive body to disengage from the drive body.

18. The injection device according to claim 16, wherein the drive body comprises a recess for receiving a head part of the coupling member to engage the coupling member with the drive body, and wherein the control member prevents movement of the head part out of the recess until the clutch reaches the stop position.

19. The injection device according to claim 16, wherein the head part and/or the recess comprises a ramp formation to bias the head part out of the recess upon relative movement of the drive body and the clutch.

20. The injection device according to claim 16, wherein the control member comprises a control surface for engagement with the coupling member and a recess on a distal side of the control surface for receiving the coupling member when the clutch reaches the stop position.

21. The injection device according to claim 12, wherein the driveshaft is provided with a clutch plate, and wherein the clutch is arranged to engage with the clutch plate when the clutch is in the locked position and to disengage from the clutch plate when the clutch is in the unlocked position.

22. The injection device according to claim 21, wherein the clutch comprises at least one engagement pin for engagement with the clutch plate.

23. The injection device according to claim 22, wherein the clutch plate includes at least one recess for receiving the at least one engagement pin.

24. The injection device according to claim 22, wherein, when the clutch is in the locked position, the at least one engagement pin extends through the drive body.

25. An injection device for delivery of a medicament from a container having a stopper for containing the medicament within the container, the device comprising:
a housing for receiving the container;
a drive body;
a driveshaft arranged for rotation with respect to the drive body;
a plunger arranged for axial movement with respect to the drive body to move the stopper towards a distal end of the container upon rotation of the driveshaft;
a drive spring arranged to apply a rotational force to the driveshaft,
the drive spring being housed within the drive body;
a clutch moveable with respect to the drive body between a locked position in which the clutch blocks rotation of the driveshaft and an unlocked position in which the driveshaft can rotate;
a coupling member comprising coupling fingers arranged to engage with the drive body to hold the clutch in the locked position and to disengage from the drive body to allow the clutch to move to the unlocked position; and
a control member comprising a sleeve cooperable with the coupling member to prevent disengagement of the coupling member from the drive body when the drive body is in a first position relative to the control member and to release the coupling member to disengage from the drive body when the drive body is in a second position relative to the control member.

26. The injection device according to claim 25, wherein the coupling member is attached to the clutch.

27. The injection device according to claim 25, wherein the drive body comprises a recess for receiving a head part of the coupling member to engage the coupling member with the drive body, and wherein the control member prevents movement of the head part out of the recess when the drive body is in the first position relative to the control member.

28. The injection device according to claim 27, wherein the head part is biased to move out of the recess when the drive body is in the second position relative to the control member.

29. The injection device according to claim 25, wherein the control member comprises a control surface for engagement with the coupling member when the drive body is in the first position relative to the control member and a recess adjacent to the control surface for receiving the coupling member when the drive body is in the second position relative to the control member.

30. The injection device according to claim 25, wherein movement of the clutch from the locked position to the unlocked position is axial with respect to the drive body, and wherein the coupling member moves radially with respect to the drive body to disengage from the drive body.

31. The injection device according to claim 25, wherein the control member is fixed with respect to the housing, and wherein the drive body is movable with respect to the housing.

32. The injection device according to claim 25, wherein the driveshaft is provided with a clutch plate, and wherein the clutch is arranged to engage with the clutch plate when the clutch is in the locked position and to disengage from the clutch plate when the clutch is in the unlocked position.

33. The injection device according to claim 32, wherein the clutch comprises at least one engagement pin for engagement with the clutch plate.

34. The injection device according to claim 33, wherein the clutch plate includes at least one recess for receiving the at least one engagement pin.

35. The injection device according to claim 33, wherein, when the clutch is in the locked position, the at least one engagement pin extends through the drive body.

\* \* \* \* \*